US012784882B2

(12) United States Patent
Reilly et al.

(10) Patent No.: US 12,784,882 B2
(45) Date of Patent: Nov. 3, 2026

(54) DIGITAL STORAGE STETHOSCOPE AND METHOD OF STORING A DATA FILE WITH SAME

(71) Applicant: Applied Integration LLC, Akron, OH (US)

(72) Inventors: Kevin P. Reilly, Pittsburgh, PA (US); Frederick J. Pingal, Tucson, AZ (US)

(73) Assignee: Applied Integration LLC, Akron, OH (US)

(*) Notice: Subject to any disclaimer, the term of this patent is extended or adjusted under 35 U.S.C. 154(b) by 234 days.

(21) Appl. No.: 18/754,290

(22) Filed: Jun. 26, 2024

(65) Prior Publication Data

US 2025/0006321 A1 Jan. 2, 2025

Related U.S. Application Data

(60) Provisional application No. 63/523,405, filed on Jun. 27, 2023.

(51) Int. Cl.

*G16H 10/60* (2018.01)
*A61B 5/00* (2006.01)
*A61B 7/04* (2006.01)

(52) U.S. Cl.

CPC ............. *G16H 10/60* (2018.01); *A61B 5/746* (2013.01); *A61B 7/04* (2013.01); *A61B 2560/0219* (2013.01); *A61B 2560/0475* (2013.01)

(58) Field of Classification Search

CPC .......... G16H 10/60; A61B 5/746; A61B 7/04; A61B 2560/0219; A61B 2560/0475

See application file for complete search history.

(56) References Cited

U.S. PATENT DOCUMENTS

| | | | | |
|---|---|---|---|---|
| 8,243,940 | B2 | 8/2012 | Smith | |
| 8,275,140 | B2 | 9/2012 | Smith | |
| 10,702,239 | B1 * | 7/2020 | McLane | G16H 40/60 |
| 12,380,973 | B1 * | 8/2025 | Venkatraman | A61B 7/04 |
| 2008/0219464 | A1 | 9/2008 | Smith | |
| 2009/0316925 | A1 * | 12/2009 | Eisenfeld | H04R 1/46 381/67 |

(Continued)

OTHER PUBLICATIONS

Website: https://www.thinklabs.com/—Thinklabs One Digital Stethoscope, Jun. 26, 2024.

*Primary Examiner* — Paul W Huber

(74) *Attorney, Agent, or Firm* — The Powers IP Law Firm

(57) ABSTRACT

A digital storage stethoscope is provided. The digital storage stethoscope includes a noise canceling microphone apparatus configured to detect an analog signal from a sound generating source, an amplifier electrically connected to the noise canceling microphone apparatus and configured to amplify and add electrical gain to the analog signal from the noise canceling microphone apparatus, an analog to digital converter electrically connected to the amplifier and configured to: a) receive the analog signal, b) convert the analog signal to a digital signal, and c) add digital gain to the digital signal, a controller electrically connected to the converter and configured to receive the digital signal from the converter into a data file, a memory storage electrically connected to the controller for storing the data file, and a data transmitter electrically connected to the controller and being configured to transmit the data file from the controller.

18 Claims, 2 Drawing Sheets

(56) References Cited

U.S. PATENT DOCUMENTS

| | | | | |
|---|---|---|---|---|
| 2012/0310115 | A1* | 12/2012 | Bedingham | A61B 7/04 600/586 |
| 2014/0276133 | A1* | 9/2014 | Schriefl | A61B 5/0205 600/484 |
| 2016/0262717 | A1 | 9/2016 | Smith | |
| 2018/0338732 | A1* | 11/2018 | Chiao | A61B 5/681 |
| 2019/0239819 | A1* | 8/2019 | Chang | A61B 7/003 |
| 2021/0249032 | A1 | 8/2021 | Smith et al. | |
| 2022/0079549 | A1* | 3/2022 | Hussain | A61B 7/04 |
| 2022/0323041 | A1* | 10/2022 | Chen | H04R 1/46 |
| 2024/0032875 | A1* | 2/2024 | Bedingham | A61B 7/04 |
| 2024/0341717 | A1* | 10/2024 | Friedman | H04R 1/46 |

* cited by examiner

DIGITAL STORAGE STETHOSCOPE AND METHOD OF STORING A DATA FILE WITH SAME

CROSS REFERENCE TO RELATED APPLICATION

This application claims priority to and claims the benefit of U.S. Provisional Application Ser. No. 63/523,405, filed Jun. 27, 2023, the contents of which are incorporated herein by reference in their entirety.

BACKGROUND

Stethoscopes are acoustic medical devices used for listening to internal sounds of animal or human bodies. For example, stethoscopes may be used to listen to the sounds made by the heart, lungs or intestines, as well as blood flow in arteries and veins. Stethoscopes can also be used to check scientific vacuum chambers for leaks and for various other small-scale acoustic industrial monitoring tasks. Typically, stethoscopes are used by physicians, who are trained to listen for certain sounds. Additionally, physicians typically listen to different parts of the human or animal body for a period of time with their stethoscopes, and then either make a few notes in a file about what they heard, or do not record such information. Today's stethoscopes and methods of using and working with the same suffer from a number of drawbacks, including that information discerned by users (e.g., physicians) is often not properly recorded and analyzed, and also that it often requires trained users to use such devices.

It is with respect to these and other considerations that the instant disclosure is concerned.

SUMMARY

In one aspect of the disclosed concept, a digital storage stethoscope is provided. The digital storage stethoscope includes a noise canceling microphone apparatus configured to detect an analog signal from a sound generating source, an amplifier electrically connected to the noise canceling microphone apparatus and configured to amplify and add electrical gain to the analog signal from the noise canceling microphone apparatus, an analog to digital converter electrically connected to the amplifier and configured to: a) receive the analog signal, b) convert the analog signal to a digital signal, and c) add digital gain to the digital signal, a controller electrically connected to the converter and configured to receive the digital signal from the converter into a data file, a memory storage electrically connected to the controller for storing the data file, and a data transmitter electrically connected to the controller and being configured to transmit the data file from the controller.

In another aspect of the disclosed concept, a method of storing a data file with the aforementioned digital storage stethoscope is provided.

DETAILED DESCRIPTION OF THE PREFERRED EMBODIMENTS

As will be employed herein, the term "coupled" shall mean connected together either directly or through one or more intermediate parts or components.

As employed herein, the phrase "digital signal processing" shall mean processing digitized data through computers or more specialized signal processors to perform a wide variety of signal processing operations. Digital signal processing may be performed in time domain (one-dimensional signals), spatial domain (multidimensional signals), frequency domain, and wavelet domain. Non-limiting examples of digital signal processing include min/max analysis, Bilinear transform, Discrete Fourier transform, Discrete-time Fourier transform, Filter design, Goertzel algorithm, Least-squares spectral analysis, LTI system theory, Minimum phase, s-plane, Transfer function, and Z-transform.

As employed herein, the phrase "computational device" shall mean a device that is configured to perform digital signal processing. Non-limiting examples of computational devices in accordance with the disclosed concept include smart devices (e.g., phones and watches), computers, tablets, and servers (e.g., data servers).

As employed herein, the phrase "noise canceling microphone apparatus" may include a microphone apparatus that is configured to: a) receive at least two sources of sound; b) phase shift one of the two received sources of sound (e.g., optionally phase 180 degrees); and c) blend the phase shifted source of sound back in with at least one of the other initially received sources of sound. Noise canceling microphone apparatus in accordance with the disclosed concept may include at least two individual microphones, wherein a first of the microphones is configured to listen to a localized region of a sound generating source, and a second of the microphones is configured to listen to ambient noise.

Figure 1:
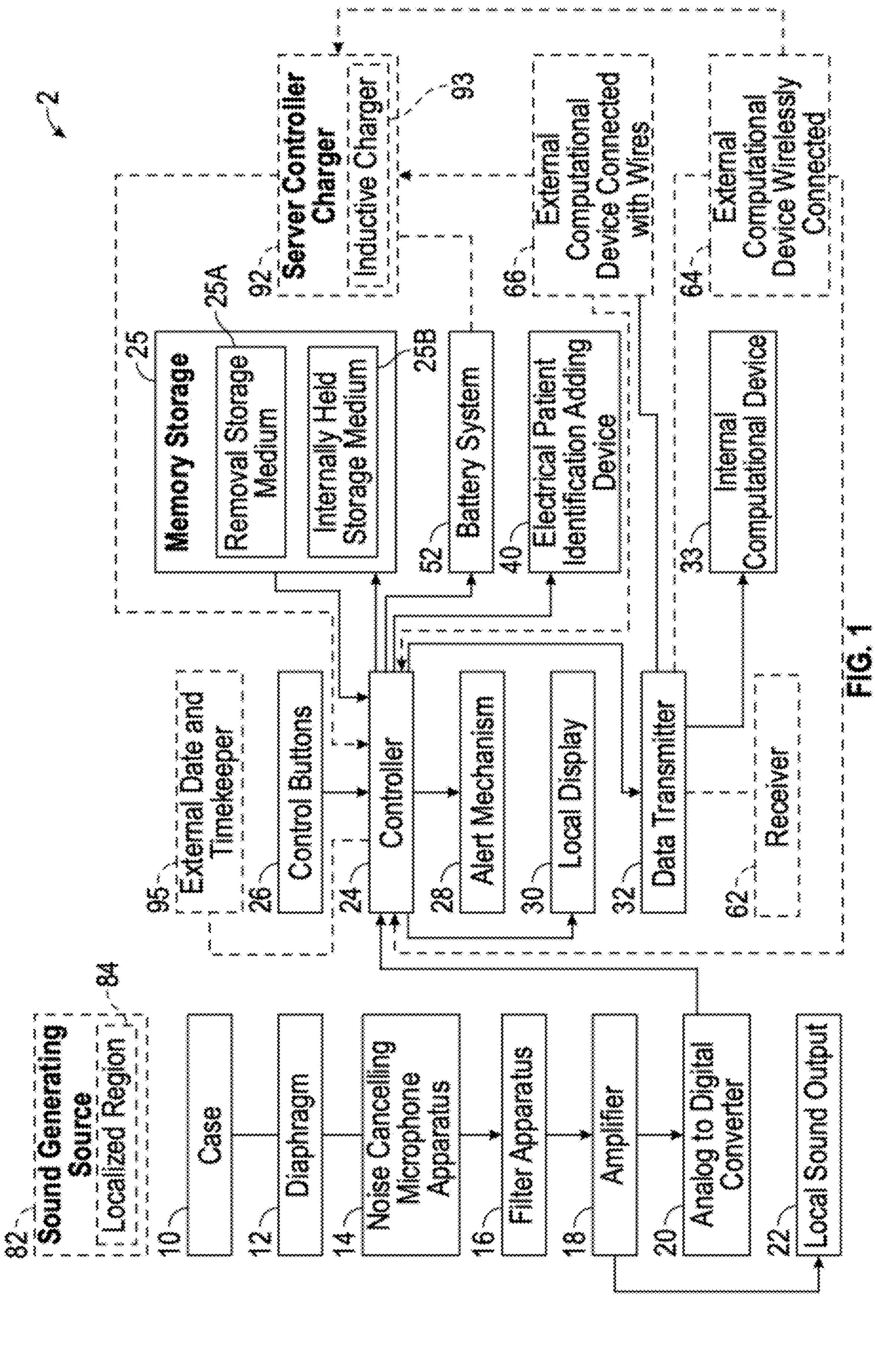
FIG. 1 is a block diagram of a digital storage stethoscope, where dashed lines and dashed boxes indicate elements configured to be employed or associated with the digital storage stethoscope, in accordance with one non-limiting embodiment of the disclosed concept.

In accordance with one non-limiting embodiment of the disclosed concept, a digital storage stethoscope 2 is provided, as shown schematically in FIG. 1. Stethoscope 2 has numerous advantages over prior art stethoscopes. First, as will be discussed below, rather than only being able to be used by trained physicians who know what to listen for, stethoscope 2 advantageously is able to be used by relatively low paid medical personnel, such as nurses or technicians who may be assisting a physician. Specifically, without needing to listen for specific sound patterns, nurses, technicians, and other personnel can simply place stethoscope 2 on the body of a patient or animal, and allow sound data to be recorded. In this manner, physician time can be made more efficient. Second, as stethoscope 2 is a digital storage stethoscope, sound data emanating from inside the patient or animal, such as the sounds of the heart, lungs, intestines, arteries, veins, etc., is advantageously able to be recorded, digitized, and stored. Stethoscope 2 thus does a significantly better job of preserving sound information (e.g., digitizing it) and allowing it to be used in treatments by future personnel (e.g., physicians, nurses, etc.), as compared to today's devices and methods, wherein sound information may be written down by a physician, not stored in a central database, or not be recorded at all.

In order to achieve these benefits, stethoscope 2, as shown in FIG. 1, preferably includes a case 10, a diaphragm 12 coupled to case 10, a noise canceling microphone apparatus 14 coupled to diaphragm 12, and a filter apparatus 16 electrically connected to noise canceling microphone apparatus 14. In one non-limiting example, diaphragm 12 is coupled to noise canceling microphone apparatus 14 via an air chamber, and is configured to add mechanical gain to a detected sound signal from sound generating source 82 before the analog signal has been created. More specifically, in one example, sound may enter stethoscope 2 through a relatively large diameter diaphragm 12, and then amplify the sound by coupling the sound to a relatively small opening in front of noise canceling microphone apparatus 14, such that an area difference between large and small openings allows gain to be obtained.

Moreover, in accordance with the disclosed concept, diaphragm 12 may be a physical gain amplifier cone. Furthermore, filter apparatus 16 may include either: a) an analog filter electrically connected to amplifier 18, and/or b) a digital filter electrically connected to noise canceling microphone apparatus 14. In one preferred embodiment, filter apparatus 16 includes the analog filter electrically connected to noise canceling microphone apparatus 14. As such, filter apparatus 16 may be configured as an adjustable width band pass filter, a low pass filter, a high pass filter, or an all-pass filter in order to localize sound within a predetermined frequency range.

In operation, ambient noise may enter stethoscope 2, but will substantially or entirely be prevented from passing into the electronics of stethoscope 2 due to noise canceling microphone apparatus 14 being, in one example, configured to cancel ambient noise. Accordingly, when an operator (e.g., physician, nurse, technician, etc.) places stethoscope 2 on the patient or animal, noise canceling microphone apparatus 14 is configured to detect sound from within the patient or animal through diaphragm 12, which may have a patient-friendly coating (e.g., rubber). When this is done, an analog signal of, for example, a heartbeat, is passed into filter apparatus 16.

By employing filter apparatus 16, stethoscope 2 advantageously is configured to increase gain on very precise frequency bands of detection. This is beneficial because certain sounds which are of concern, such as the beat of a heart, are often localized in sound frequency. Thus, it is desirable that these sounds be recorded. As such, other miscellaneous sounds such as blood vessels, harmonics, etc., are unable to affect the recorded signal. This is generally not possible with standard stethoscopes, wherein such devices cannot avoid hearing the sounds of the harmonics, blood vessels, etc.

Stethoscope 2 also preferably includes an amplifier 18 electrically connected to filter apparatus 16, an analog to digital converter 20 electrically connected to amplifier 18, and a local sound output 22 electrically connected to amplifier 18, optionally connected via a wire or wires. In accordance with the disclosed concept, amplifier 18 amplifies and adds electrical gain to the analog signal exiting filter apparatus 16 and passes it to analog to digital converter 20 and local sound output 22. Analog to digital converter 20 is configured to: a) receive the analog signal, b) convert the analog signal to a digital signal, and c) add digital gain to the digital signal, as will be discussed below.

By passing the signal to local sound output 22, a user, if desiring to do so, can connect headphones or other modern listening mechanisms (e.g., electrically or wirelessly) to local sound output 22 and listen to a live analog signal of sound of the detected region. It will, however, be appreciated that suitable alternative stethoscope devices within the scope of the disclosed concept need not include such an output, but rather can rely on wireless transfer of the signal, as will be discussed below.

Continuing to refer to FIG. 1, stethoscope 2 further includes a controller 24 electrically connected to analog to digital converter 20, and functioning at least in part to direct the digital signal being sent to it from analog to digital converter 20. In one example, controller 24 is a microcontroller. Stethoscope 2 may also include a memory storage 25 electrically connected to controller 24 for storing data sent from analog to digital converter 20. In one example, memory storage 25 includes either a removal storage medium 25A and/or an internally held storage medium 25B. Data files disclosed herein may also be stored at external computational devices 64,66 via data transmitter 32, as will be discussed below.

Additionally, in one example embodiment, stethoscope 2 further has control buttons 26 (e.g., volume adjustment buttons, on/off buttons, pair to external devices buttons, etc.) electrically connected to controller 24 and configured to allow a user to locally control operations of controller 24. Furthermore, stethoscope 2 also preferably includes an alert mechanism 28 electrically connected to controller 24, and a local display 30 electrically connected to controller 24, wherein local display 30 is configured to display at least an amplitude of the detected sound signal (e.g., either from the analog signal or the digital signal).

Alert mechanism 28 provides stethoscope 2 with the capability of being aligned over desired detection regions. For example, alert mechanism 28 may be configured to alert a user that stethoscope 2 is either properly positioned or improperly positioned with respect to a localized region 84 (FIG. 1) associated with a sound generating source 82 (FIG. 1), wherein sound generating source 82 may be a heart, lungs, other sound source of a living body, as well as sound from a non-living body (e.g., a mechanical engine).

Accordingly, controller 24 may be configured to have firmware integrated therein to detect when diaphragm 12 is properly positioned. Furthermore, when positioning is proper, the electrical connection between diaphragm 12 and alert mechanism 28 causes a corresponding alert being generated. In one example, alert mechanism 28 may include a local sound alert mechanism configured emit an audio signal responsive to stethoscope 2 being either properly positioned or improperly positioned with respect to localized region 84. In another example, alert mechanism 28 includes a light source configured to emit visible light (e.g., an LED or other light source, which is electrically connected to controller 24, lights up to alert a user) responsive to stethoscope 2 being either properly positioned or improperly positioned with respect to localized region 84.

Stethoscope 2 may also, in one example embodiment, further have a data transmitter 32 electrically connected to controller 24. Data transmitter 32 is configured to transmit a data file from controller 24 (e.g., a data file containing a recorded digital signal of sound received from analog to digital converter 20) to: a) a computational device (e.g., either an internal computational device 33 or one or both of external computational devices 64, 66) for performing digital signal processing, and/or b) a receiver 62 for listening. Additionally, as shown in FIG. 1, internal computational device 33 is preferably electrically connected to data transmitter 32 and is configured to receive and process the data file of the digital signal from data transmitter 32. Internal computational device 33 is preferably located internal with respect to stethoscope 2 (e.g., internal with respect to case 10) and is an integral component of stethoscope 2.

In operation, noise canceling microphone apparatus 14 is preferably configured to detect an analog signal from sound generating source 82 (FIG. 1). Next, amplifier 18 is configured to amplify the analog signal from noise canceling microphone apparatus 14, and analog to digital converter 20 is configured to receive the analog signal and convert the analog signal to a digital signal. This conversion advantageously allows for later processing of the initial sound from sound generating source 82. Subsequently, controller 24 receives the digital signal from analog to digital converter 20 into a data file, memory storage 25 stores the data file, and data transmitter 32 is configured to transmit the data file from controller 24.

Additionally, as shown in FIG. 1, data transmitter 32 is preferably configured to wirelessly transmit the stored data file to receiver 62 (e.g., a receiver associated with headphones). Moreover, data transmitter 32 is also configured to wirelessly transmit the aforementioned data file to external computational device 64 (e.g., a data server), and also transmit the data file via a wired connection to another external computational device 66 (e.g., a data server, computer, etc.). In one example, each of computational devices 64, 66 are positioned external with respect to stethoscope 2. Connections to external computational devices 64, 66 and/or storage inside stethoscope 2 itself advantageously allows for continuous monitoring via removable SD chips and/or in client server environments. In one example, each of external computational devices 64,66 is preferably configured to program and control stethoscope 2, either wirelessly or via wired connections. This may present as users employing external computational devices 64,66 to program controller 24 in order to configure and setup stethoscope 2, e.g., change filter settings, patient data, etc.

Once digital data files of detected patient or animal regions is sent from controller 24 to data transmitter 32, the data files may be passed out of stethoscope 2 in at least one of the following ways, in accordance with the disclosed concept. First, via wireless connection to receiver 62, if a user has, for example, air/ear pods, blue tooth devices, or other wireless listening devices (e.g., speakers), that the user can connect to receiver 62 and listen to the sound of the detected region of the patient or animal, at an instance in time after the initial sound was detected and recorded, or in real-time. Second, via wireless connection to external computational device 64 and/or wired connection to external computational device 66, the data can be sent to either off-site servers (e.g., cloud for access via a device such as a smartphone, tablet, and/or computer on an app) or on-site servers, respectively, wherein digital signal processing or recording on such devices may be performed.

At this point, the data can be controlled and processed, as well as listened to and recorded. By having the data accessible in this manner, unlike today's methods, physicians and personnel may better be able to predict, and therefore help stop, future medical problems by readily having access to this information. For example, artificial intelligence may be used to analyze this sound data easily, thereby allowing even the most minimally trained personnel acquire professional results. This occurs when computational devices (e.g., servers) both analyze and aggregate all the sounds digitized by stethoscope 2 so that there becomes a large body of knowledge of human heart and other sounds over time. This is where artificial intelligence again is used to model the soundscape of the human bodily functions, in this case the heart. The order of magnitude of recorded sounds will be significantly large, potentially more than trillions.

Furthermore, analysis of collected data can be accomplished anywhere in the universe (e.g., if data is being collected from a patient or animal in country A, a physician or other personnel in country B will readily be able to analyze the data as it is being collected, thereby significantly improving the capacity of medical personnel to treat patients). Additionally, it will be appreciated that file storage types of collected data are HIPPA compliant, thus protecting patient sensitive information. Moreover, sound data can be stored for later retrieval, archiving, education, aggregate data analysis, etc. It will further be appreciated that in, for example, a hospital setting, a single person such as a nurse may be able to monitor an entire floor by having different digital storage stethoscopes like stethoscope 2 strapped to patients. Further yet, stethoscope 2 may be issued to patients for overnight or long-term recording, thus eliminating the need for a hospital stay and continual nursing.

As shown in FIG. 1, stethoscope 2 may further include an electrical patient identification adding device 40, which may be a barcode reader, a QR code reader, an RF ID reader, a DNA sensor, etc., wherein electrical patient identification adding device 40 may be configured to scan an identification of a patient associated with stored records. For example, a nurse may employ electrical patient identification adding device 40 to scan an identification bracelet being worn by a patient, such that stored records (e.g., in a data server, cloud, or the like) may be retrieved and associated with any signals detected on said patient with stethoscope 2.

Furthermore, FIG. 1 also shows stethoscope 2 as including a battery system 52 electrically connected to controller 24, and configured to supply power to stethoscope 2. Additionally, stethoscope 2 is shown in FIG. 1 as employed with a server controller charger 92, which may be, for example and without limitation, a smart charging station and operational adjustment system (e.g., without limitation, a newly built charging station, a smart phone, a tablet, etc.) that functions to charge stethoscope 2 (e.g., when docked) and also allow parameters of stethoscope 2 to be adjusted. This charging may allow stethoscope 2 to function for extended periods of time. In one example embodiment, this period of time may be up to at least 8 hours. Accordingly, it will be appreciated that the disclosed concept may provide for an assembly kit comprising server controller charger 92 and stethoscope 2 configured to be electrically connected to server controller charger 92. Moreover, in one example, server controller charger 92 includes an inductive charger 93 for inductively charging battery system 52. It will also be appreciated that mechanical charging of battery system 52 is contemplated.

Accordingly, it will be appreciated that a principal operation of stethoscope 2 is to take analog sound input, digitize it and perform a suite of digital signal processing techniques including, but not limited to, derivatives, fast fourier transforms, integrals, graphing, etc. The digitized sound can then be stored, categorized, and correlated to relate the sound and processed signals to disease or health states then used with artificial intelligence to predict future health or disease states. It will be appreciated that stethoscope 2 is preferably configured to detect and digitize sound from frequencies of 0 hertz to 30,000 hertz.

Moreover, it will be appreciated that in one non-limiting example, stethoscope 2 includes noise canceling microphone apparatus 14, amplifier 18, analog to digital converter 20, controller 24, memory storage 25, and data transmitter 32 as required elements, with other elements (e.g., without limitation, case 10, diaphragm 12, local sound output 22, electrical patient identification adding device 40, etc.)

depicted in FIG. 1 being optional additional elements. Other examples are contemplated herein.

Figure 2:
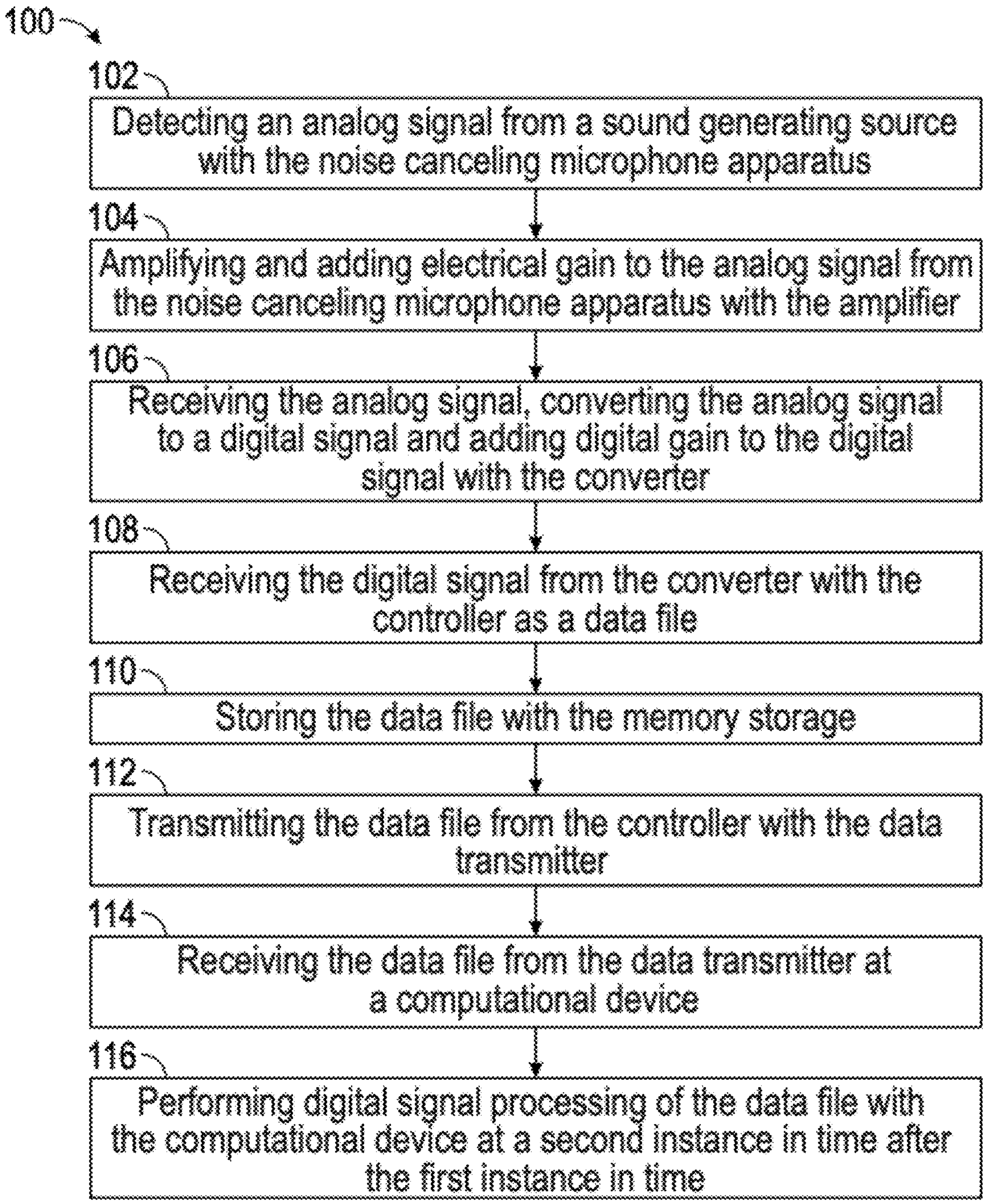
FIG. 2 is a flow diagram corresponding to an example method of storing data with the digital storage stethoscope of FIG. 1.

FIG. 2 shows an example method 100 of storing data with digital storage stethoscope 2. As shown, method 100 may include a first step 102 of detecting an analog signal, a second step 104 of amplifying and adding electrical gain to the analog signal, a third step 106 of receiving the analog signal, converting the analog signal, and adding digital gain to the converted digital signal, a fourth step 108 of receiving the digital signal from converter 20, a fifth step 110 of storing the data file with memory storage 25, a sixth step 112 of transmitting the data file, a seventh step 114 of receiving the data file from data transmitter 32, an eighth step 116 of performing digital signal processing of the data file with a computational device 33, 64, 66, a ninth step of sending a date and a patient number to controller 24 from an external date and timekeeper 95 (FIG. 1) before transmission from data transmitter 32, a tenth of charging battery system 52 with an inductive charger 93 of a server controller charger 92, and an eleventh step of sending instructions to controller 24 from an external computational device 64,66 in order to remotely control the stethoscope.

While this disclosure has been described as having exemplary methods, the present disclosure can be further modified within the spirit and scope of this disclosure. This application is therefore intended to cover any variations, uses, or adaptations of the disclosure using its general principles. For example, though this application has been described in association with stethoscope 2 including multiple methods of passing digital data of patient sounds, any number (e.g., 1, 2, etc.) of methods are contemplated. Further, this application is intended to cover such departures from the present disclosure as come within known or customary practice in the art to which this disclosure pertains and which fall within the limits of the appended claims.

What is claimed is:

1. A digital storage stethoscope comprising:

a noise canceling microphone apparatus configured to detect an analog signal from a sound generating source;

a filter apparatus electrically connected to the noise canceling microphone apparatus and configured to receive the analog signal from the noise canceling microphone apparatus, the filter apparatus being configured to increase gain on precise frequency bands of detection of the analog signal in order to localize sound from the sound generating source within a predetermined frequency range;

an amplifier electrically connected to the noise canceling microphone apparatus via the filter apparatus and configured to amplify and add electrical gain to the analog signal from the noise canceling microphone apparatus after the analog signal has been directed to the amplifier by the filter apparatus;

an analog to digital converter electrically connected to the amplifier and configured to: a) receive the analog signal, b) convert the analog signal to a digital signal, and c) add digital gain to the digital signal;

a controller electrically connected to the converter and configured to receive the digital signal from the converter into a data file;

a memory storage electrically connected to the controller for storing the data file; and a data transmitter electrically connected to the controller and being configured to transmit the data file from the controller to a computational device for later performing digital signal processing on the data file.

2. The digital storage stethoscope according to claim 1, wherein the filter apparatus comprises an analog filter.

3. The digital storage stethoscope according to claim 1, wherein the data transmitter is configured to transmit the data file from the controller to a receiver for listening.

4. The digital storage stethoscope according to claim 3, wherein the data transmitter is configured to transmit the data file from the controller to the computational device, wherein the digital storage stethoscope further comprises the computational device, and wherein the computational device is electrically connected to the data transmitter.

5. The digital storage stethoscope according to claim 3, wherein the data transmitter is configured to transmit the data file from the controller to the computational device, wherein the computational device is positioned external with respect to the digital storage stethoscope, and wherein the data transmitter is either configured to: a) wirelessly transmit the data file from the controller, or b) transmit the data file from the controller via a wired connection between the data transmitter and the computational device.

6. The digital storage stethoscope according to claim 3, wherein the data transmitter is configured to wirelessly transmit the data file from the controller to the receiver for listening.

7. The digital storage stethoscope according to claim 1, further comprising a local sound output electrically connected to the amplifier and configured to be electrically connected to a listening mechanism for listening to the analog signal.

8. The digital storage stethoscope according to claim 1, further comprising a diaphragm coupled to the noise canceling microphone apparatus via an air chamber and configured to add mechanical gain to a detected sound signal from the sound generating source before the analog signal has been created.

9. The digital storage stethoscope according to claim 8, further comprising an alert mechanism electrically connected to the controller, and wherein, responsive to the digital storage stethoscope being properly positioned with respect to a localized region associated with the sound generating source, an electrical connection between the diaphragm and the alert mechanism causes an alert to be generated.

10. The digital storage stethoscope according to claim 1, further comprising a local display electrically connected to the controller and configured to display at least an amplitude of either the analog signal or the digital signal.

11. The digital storage stethoscope according to claim 1, further comprising control buttons electrically connected to the controller and configured to allow a user to locally control operations of the controller.

12. The digital storage stethoscope according to claim 1, further comprising an electrical patient identification adding device electrically connected to the controller and configured to scan an identification associated with stored records.

13. The digital storage stethoscope according to claim 1, further comprising a battery system electrically connected to the controller and configured to be charged by a server controller charger in order to power the digital storage stethoscope.

14. The digital storage stethoscope according to claim 1, wherein the memory storage comprises a removal storage medium or an internally held storage medium.

15. A method of storing data with a digital storage stethoscope, the digital storage stethoscope comprising a noise canceling microphone apparatus, a filter apparatus electrically connected to the noise canceling microphone apparatus, an amplifier electrically connected to the noise canceling microphone apparatus via the filter apparatus, an analog to digital converter electrically connected to the noise canceling microphone apparatus, a controller electrically connected to the converter, a memory storage electrically connected to the controller, and a data transmitter electrically connected to the controller, the method comprising:

- detecting an analog signal from a sound generating source with the noise canceling microphone apparatus;
- employing the filter apparatus to receive the analog signal from the noise canceling microphone apparatus, and increase gain on precise frequency bands of detection of the analog signal in order to localize sound from the sound generating source within a predetermined frequency range;
- amplifying and adding electrical gain to the analog signal from the noise canceling microphone apparatus with the amplifier after the analog signal has been directed to the amplifier by the filter apparatus;
- receiving the analog signal, converting the analog signal to a digital signal, and adding digital gain to the digital signal, with the converter;
- receiving the digital signal from the converter with the controller as a data file;
- storing the data file with the memory storage; and
- transmitting the data file from the controller with the data transmitter to a computational device for later performing digital signal processing on the data file.

16. The method according to claim 15, further comprising:

- sending a date and a patient number to the controller from an external date and timekeeper.

17. The method according to claim 15, wherein the digital storage stethoscope further comprises a battery system electrically connected to the controller, and wherein the method further comprises:

- charging the battery system with an inductive charger of a server controller charger.

18. The method according to claim 15, further comprising:

- sending instructions to the controller from the computational device in order to remotely control the stethoscope.

* * * * *